United States Patent [19]

Factor et al.

[11] 4,097,538

[45] Jun. 27, 1978

[54] DEHYDROCHLORINATION OF A DIHYDROXYDIPHENYL TRICHLOROETHANE

[75] Inventors: Arnold Factor, Scotia; Michael R. MacLaury, Rexford; Jimmy L. Webb, Ballston Lake, all of N.Y.

[73] Assignee: General Electric Company, Schenectady, N.Y.

[21] Appl. No.: 771,208

[22] Filed: Feb. 23, 1977

[51] Int. Cl.$^2$ .............................................. C07C 37/00
[52] U.S. Cl. .................................. 568/726; 260/591; 260/613 R; 260/649 R; 568/723; 568/725
[58] Field of Search ............ 260/613 R, 619 A, 649 R

[56] References Cited

FOREIGN PATENT DOCUMENTS

| 70,073 | 9/1975 | Poland .............................. 260/619 A |
| 1,147,258 | 4/1969 | United Kingdom ............ 260/654 D |

OTHER PUBLICATIONS

Weygand, "Prep. Org. Chem.", 4th Edition, pp. 819–822 (1974), John Wiley & Sons.

*Primary Examiner*—Norman Morgenstern
*Attorney, Agent, or Firm*—Joseph T. Cohen; Charles T. Watts

[57] ABSTRACT

1,1,1-Trichloro-2,2-bis(4-hydroxyphenyl)ethane can be dehydrohalogenated to 1,1-dichloro-2,2-bis(4-hydroxyphenyl)ethylene by treating the former with liquid ammonia.

3 Claims, No Drawings

DEHYDROCHLORINATION OF A DIHYDROXYDIPHENYL TRICHLOROETHANE

This invention is concerned with a process for dehydrohalogenating a dihydroxydiphenyl trichloroethane. More particularly, the invention is concerned with a process for obtaining in good yield and purity the compound 1,1-dichloro-2,2-bis(4-hydroxyphenyl)ethylene (hereinafter referred to as "dichloride") having the formula

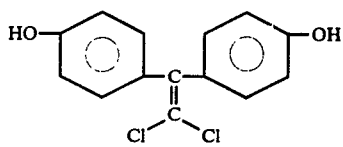

by treating 1,1,1-trichloro-2,2-bis(4-hydroxyphenyl)ethane (hereinafter referred to as "trichloride") having the formula

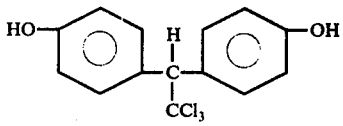

with liquid ammonia.

In a broader sense, this invention is concerned with a process of dehydrohalogenating trichloride compounds of the general formula

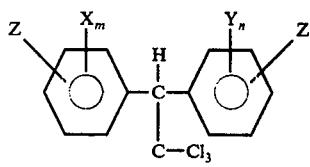

to the corresponding dichloroethylene compound where Z is a member selected from the class consisting of HO—, $CH_3O$—, and Cl, and may be ortho, meta, or para to the >CH—$CCl_3$ group, X and Y are the same or different members selected from the class consisting of halogen and alkyl groups of from 1 to 3 carbon atoms, and m and n are whole numbers equal to from 1 to 4 inclusive. Among the compounds which may be employed coming within the scope of formula III may be mentioned those having the formulas

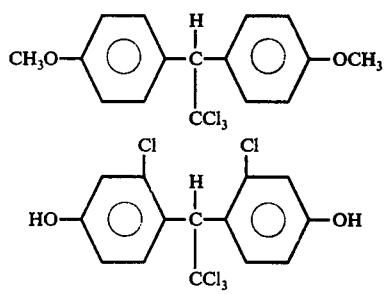

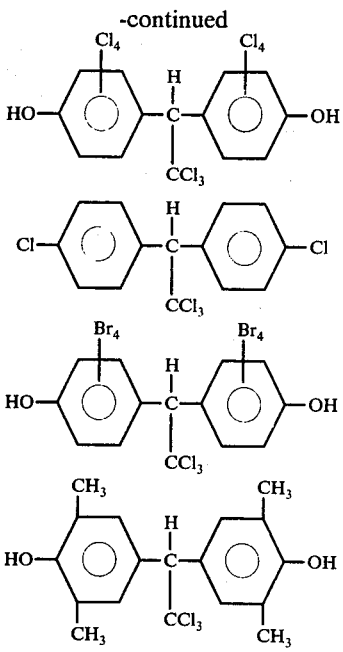

The dehydrochlorination of the aforesaid trichloride to the dichloride is reported in numerous publications. M. Trojna and J. Hubacek, Chem. Listy 51, 752 (1957) [also described in Chemical Abstracts 51, 11297a (1957)] treated the trichloride with a large molar excess of aqueous sodium hydroxide at elevated temperatures to obtain a 35% yield of the dichloride. Hubacher, in J. Org. Chem. 24, 1949 (1959), reported an improved dehydrochlorination procedure using 6 mole equivalents of KOH in methanol to give a 74% yield of the dichloride that was pale yellow in color.

S. Porejko and Z. Wielgosz, in the publication Polimery 13, 55 (1968) improved the dehydrochlorination technique by lowering the reaction temperature and using 15 mole equivalents of KOH in methanol to give a 90% yield of the dichloride. The Polish Pat. No. 144,765 of Wielgosz, Krajewski, and Rawski, published Sept. 8, 1975, effected dehydrochlorination using KOH in methanol at about 40° C. for 3 hours, followed by heating to reflux. Neutralization with acid and crystallization from water afforded a 91% yield of the dichloride. Evaluation of this latter procedure revealed that the dichloride obtained had significant amounts of impurities and was highly colored rather than white.

We have now discovered that liquid ammonia can be used to dehydrochlorinate the trichloride to the dichloride and in so doing, several advantages are derived over previously described procedures. In the first place, no additional solvent of any kind is normally required; the ammonia acts as both the reactant and the solvent medium. In order to separate the dichloride from the reaction solution, one only needs to allow the ammonia to evaporate from the reactor and recover it and store it for further use. Moreover, the dichloride obtained by this procedure after the by-product ammonium chloride is removed by methanol-water or water washes, is freer of usual impurities than the products obtained by any of the abovedescribed procedures at a similar stage of purification as measured by gradient elution high pressure liquid chromatography (HPLC). If further purification of the dichloride by crystallization from methanol-water (whose pH has been adjusted to 3-7) is used, the product obtained is as good, if not better both in color and in lack of impurities as any of the above-described procedures. What is equally significant is the fact that by using ammonia and pressure, the reaction can be run at higher temperature with little or no significant increase in impurities, thus permitting total reaction times of much shorter duration than has been possible in the past. Although a large molar excess of ammonia is used to serve both as a reactant and a solvent medium, the dehydrochlorination only uses 1 mole of ammonia per mole of trichloride, and at the end of the reaction the unused ammonia can be easily recovered by distillation (boiling point −33° C.). Thus, large amounts of acid are not needed to neutralize the reaction mixture as is needed in the KOH/methanol procedure.

In the discussion above, a number of impurities have been referred to and specifically these impurities or contaminants comprise mainly one or more of the following:

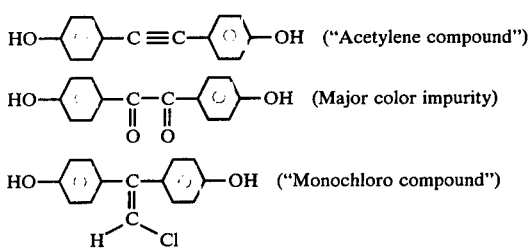

One of the achievements of our process using liquid ammonia for dehydrohalogenation purposes is the fact that the dichloride obtained needs a minimum of purification, for instance, a single or at most two recrystallizations, has exceptionally good color usually approaching almost a pure white appearance, and has a minimum of contaminants which would require removal.

One of the uses to which the dichloride of the present invention can be put is in the formation of polycarbonate resins comprising the following recurring unit:

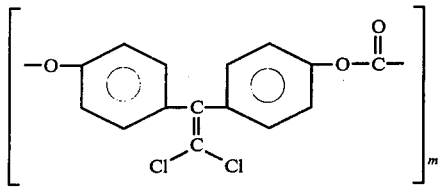

where $m$ is a whole number greater than 1. Such polymers are more particularly described in Polish Pat. No. 48,893, issued Dec. 12, 1964. It has been found that, because the dichloride prepared in accordance with the description in the aforesaid Polish Pat. No. 48,893 is not of adequate purity (as established by the number and amount of contaminants and by the color), polycarbonates made by the reaction of the dichloride and a phosgenating precursor, such as phosgene, diphenyl carbonate, etc., have impact properties which are smaller than desirable or might even be expected from the usual polycarbonates, for instance, those made from a precursor phosgenating agent and bisphenol-A. As shown in the copending application of Cleveland, Webb, and Orlando, Ser. No. 765,654 (RD-7419), filed Feb. 4, 1977 and assigned to the same assignee as the present invention, marked and unexpected improvements in impact characteristics of polycarbonate resins made from highly purified dichloride can be obtained. It is for this reason that the present invention assists in the attainment of such high impact polymers by virtue of the production of substantially pure dichloride.

As used hereinafter, the expression "substantially pure," when referring to dichloride, will signify a dichloride having an absorbance value of less than 0.3, as shown by measuring the absorbance of a methanol solution of the dichloride (2.50 gm/50 ml in a 10 cm cell) using a Carey 14 recording spectrophotometer with light at 425 nm.

A Waters Model 244 liquid chromatograph is used, equipped with a Model U6K injector, a $\mu$ $C_{18}$ Bondapak column, a Model 440 detector equipped with a 10 mm cell and operated at 280 nm set at 0.1 AUFS and a 10 millivolt Houston Instrument Omniscribe recorder with a chart speed of 0.25 centimeter per minute. Ten microliters of a 10% (wt./vol.) methanol solution of the dichloride is injected into the column and it is eluted at 2 ml per minute, where the solvent mixture is programmed linearly over a 1 hour period from an initial composition of 40% methanol and 60% water to a final composition of 100% methanol.

It has been known in the past that ammonia can be employed to dehydrochlorinate wholly aliphatic unsaturated chlorohydrocarbons to form chloroprene. In this connection, attention is directed to British Pat. No. 1,147,258, published April 2, 1969, which is typical of many references which depict the same reaction as identified by the equation

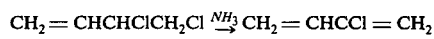

Even though ammonia had been used to effect the removal of hydrogen chloride from aliphatic unsaturated chlorinated hydrocarbons, prior to the present invention, so far as is known, such dehydrohalogenation was never attempted with a dihydric phenol such as a trichloride of formula II, nor with a diaryl compound having three chlorine atoms on one carbon atom. Moreover, no reference is known which would indicate that the use of ammonia to dehydrohalogenate the trichloride would give a dichloride of such purity under equivalent purification conditions and substantially free of contaminants when compared with prior methods of dehydrohalogenating the trichloride to the dichloride.

In accordance with our invention, the dehydrochlorination of the trichloride can be achieved by charging the trichloride to a pressure reactor together with the liquid ammonia, and thereafter heating the pressure reactor at temperatures ranging from 25° to 125° C., and preferably from 50° to 100° C., for times ranging from about 30 minutes to 6 hours or more to effect the dehydrohalogenation. Thereafter, the formed dichloride can be removed from the liquid ammonia solvent and ammonium chloride formed, by first allowing the ammonia to evaporate and collecting the latter, and then separating, by washing with water, thereby removing the ammonium chloride from the dichloride. If further purification is desired, the dichloride can then be recrystallized from a methanol-water mixture whose pH has been adjusted to 3–7 in which any impurities present in the dichloride are soluble.

The amount of ammonia used with regard to the dichloride undergoing dehydrohalogenation can be varied widely. At least one mole of the ammonia should be used per mole of trichloride. However, for optimum results, in order to attain the objective of using the ammonia both as a reactant and as a solvent medium, we have found that molar concentrations ranging from about 3 to 20 or more moles of ammonia per mole of the trichloride are advantageously employed. It is evident that the size of the pressure reactor will in many instances dictate the molar concentrations of the ammonia and the trichloride.

Depending on the temperatures and the amount of ammonia present in the pressure reactor, pressures ranging from 50 psi to 700 to 800 psi or more can be employed without materially affecting the results. Temperatures of the order of 50° to 125° C. are advantageously used; again this will depend on the type and size of the pressure reactor employed, the molar concentrations of the ammonia and the trichloride, etc. Because the reaction using the ammonia can be run at a higher temperature with little or no significant increase in impurities, total reaction times of much shorter duration are possible than with other methods for dehydrohalogenation. Thus, it has been found at 100° C. dehydrohalogenation reaction is complete in one hour compared to three hours for the KOH/methanol process described in the above-identified Polish Pat. No. 144,765.

Under the pressure conditions employed in the practice of our invention, temperature, of course, is an important function in the attainment of a substantially pure dichloride free of any by-products or of any of the starting trichloride. Thus, as one proceeds from around room temperature (about 20°-30° C.) to about 125° C., one will find that with the use of reasonable times of reaction, for instance, about 30-90 minutes, at the upper end of the temperature range, substantially all of the trichloride is converted to the dichloride in a substantially pure state and no detectable amount of trichloride is present in the final product.

Although the reaction between the ammonia and the trichloride can be carried out without any further ingredients, the use of aprotic solvents is not precluded. Included among such solvents may be mentioned dimethyl formamide, N-methyl pyrrolidone, N,N-dimethylacetamide, dimethyl sulfoxide, etc. Amounts of such solvents, for instance, by weight, from about 0.1 to 2 parts of the solvent per part of the trichloride, can be used to advantage in order to reduce the amount of excess liquid ammonia which may be required. Dimethyl sulfoxide tended to increase the rate of reaction, while N-methyl pyrrolidone dimethylacetamide had no deleterious effect on the rate compared to the use of pure ammonia. The presence of up to 10-12 weight percent water in the reaction mixture does not deleteriously affect the results.

It would also be expected that amines such as primary, secondary, and tertiary amines could be used for dehydrohalogenation purposes as has been used in the prior art. However, unexpectedly it was found that secondary and tertiary amines were very slow in effecting the dehydrohalogenation and, in addition, they caused the formation of large amounts of side products and highly colored impurities. Although the primary amines, such as methyl amine and ethyl amine were able to provide reasonable rates of reaction for dehydrohalogenation purposes, the dichloro compound obtained from these reactions was less pure and more colored than when ammonia was used itself.

In order that those skilled in the art may better understand how the present invention may be practiced, the following examples are given by way of illustration and not by way of limitation. Unless otherwise indicated, all parts are by weight.

EXAMPLE 1

About 0.3 gram of the trichloride of formula II was dissolved in about 2 ml liquid ammonia at −30° C. in a pressure reaction vessel. The reaction vessel was closed and allowed to warm to room temperature (about 25° C.) at which point the pressure inside the pressure vessel was about 140 psi. After 15 hours at room temperature while the mixture inside the pressure vessel was agitated, the reaction was completed as evidenced by the fact that when the vessel was opened up and the excess ammonia allowed to evaporate under a nitrogen stream, and the residue slurried with water and filtered, this yielded a white solid which when washed with water and dried at 110° C. in vacuum, yielded 0.25 gram of the dichloride of formula I in about a 95.2% yield.

EXAMPLE 2

100 grams of the trichloride of formula II was weighed into a glass liner which fitted into an autoclave pressure unit. Approximately 200 ml liquid ammonia was placed in the liner which was cooled in a dry ice-acetone bath. The liner was placed in the autoclave and the autoclave sealed. The autoclave was equipped with a stirrer, thermowell, diptube, and a cooling coil. The reaction was carried out at a temperature of 108° C. and a pressure of 900 psi. At the end of about 70 minutes, 100 ml methylene chloride was pumped into the autoclave and the ammonia vented off. The autoclave was opened, the liner removed and the remaining ammonia allowed to evaporate. The methylene chloride slurry was filtered and washed with additional methylene chloride followed by a water wash. This yielded 81.4 grams of substantially pure dichloride which was white in color and represented about a 92% yield of the theoretical amount.

EXAMPLE 3

450 grams of the trichloride of formula II was added to a one-gallon volume autoclave. The autoclave was cooled with liquid nitrogen to below −30° C. and 1.3 liters of ammonia were added. The autoclave was sealed and warmed to 100° C. over a period of about 1½ hours and held at 100° C. for 1 hour while agitating the mixture. The pressure at 100° C. was between 600 and 700 psi. After the 100° C. heating, the reaction solution was cooled and the ammonia slowly vented. Thereafter, the autoclave was opened to atmospheric pressure and 2 liters of 80% (by volume) aqueous methanol added to the solid product. After stirring the mixture for about 25 minutes at 40°-50° C., the solution was removed from the autoclave. At this point the aqueous methanol solution contained the desired dichloride of formula I, ammonium chloride, and about 10-15 weight percent excess ammonia. Enough water was added to the reaction mixture to double the volume and then the mixture was heated with stirring to 70°-80° C. to form a homogeneous solution, and allowed to cool slowly. The deposited crop of white crystalline product was removed in about a 90% yield and identified as almost pure dichloride of formula I.

The work-up of the reaction product can also be modified whereby the reaction mixture in the autoclave can be removed, acidified with a dilute mineral acid such as HCl or $H_2SO_4$ to a pH below 7, e.g., 3-5, diluted with water to double the starting volume, and then heating the mixture to about 70°–80° C. to form a homogeneous solution. By allowing the product to cool, again a substantially pure dichloride in about a 94% yield is obtained. The use of the mineral acids for working up the reaction product tends to produce somewhat better yields of the desired dichloride. In addition, less coloring is present in the dichloride than when a non-acidic work-up is employed. Moreover, since the trichloride of necessity because of its manner of preparation, contains a very small amount of an impurity, the orth-para-trichloride derivative having the formula

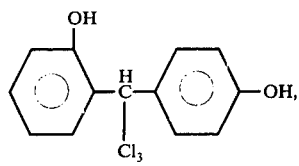

there is a tendency for the corresponding ortho-para-dichloride also to be formed; by using the basic work-up, the ortho-para-dichloride can be removed readily by crystallization from aqueous methanol rendered basic at a pH above 7, e.g., from about 9–10.

EXAMPLE 4

Employing the same ingredients, amounts of ingredients, and conditions as described in Example 3, the trichloride of formula II was reacted with ammonia, but before reaction was initiated, 60.4 grams of water was added to the trichloride. After the reaction was completed, the autoclave was vented and 2 liters of 80% (by volume) aqueous methanol was added to the solid product in the reactor. After stirring the mixture at 40°–50° C., the solution was removed from the autoclave. At this point the desired dichloride of formula I was present in the aqueous methanol solution together with ammonium chloride and the remaining ammonia. The reaction mixture was divided into two parts. One part (identified as 4a) was diluted with about double the volume of water and the mixture heated with stirring at about 70°–80° C. to form a homogeneous solution and then allowed to cool. This resulted in a deposit of a white crystalline product which was identified as almost pure dichloride of formula I. The other half of the reaction product (identified as 4b) was acidified with enough sulfuric acid to reduce the pH of the reaction product to between 5–6. Again, water was added and the mixture heated and allowed to cool similarly as was done in connection with 4a.

The following table shows the results of analyses for the acetylene and monochloro compounds conducted on dichloride prepared in the above examples as well as in similarly prepared dichloride (altering the conditions somewhat) as compared to the results obtained by following the procedures described in Polish Pat. No. 144,765.

The conditions for making the dichloride in the Polish Pat. No. 144,765 follow the single working example described in the patent. More particularly, to a solution of 1.68 parts potassium hydroxide (30 mole equivalents) and 3.12 parts methanol was introduced 1.59 parts (5 mole equivalents) of the trichloride while maintaining the temperature of the mixture at about 40° C. This combination of ingredients was stirred at 40° C. for about 3 hours, after which the mixture was heated to its boiling point and cooled to room temperature. Thereafter, about 3.5 parts of 25% hydrochloric acid was added until neutralization of the mixture was attained. The mixture was again heated to its boiling point to form a soluble solution, cooled to room temperature, and the precipitate which formed was separated, washed several times with water until essentially all traces of potassium chloride were removed. The residue was then dried at a temperature of 100°–120° C. to give a 91% yield of the dichloride.

TABLE I

| | *High Pressure Liquid Chromatographic Analysis | | |
|---|---|---|---|
| Ex. No. | **Acetylene Compound Formula IV | **Monochloro Compound Formula V | Remarks |
| 1 | 0.032 | 0.012 | Reaction 15 hrs at 25° C.; washed with H$_2$O only. |
| 2 | 0.014 | 0.008 | Reaction at 108° C. for 70 min.; CH$_2$Cl$_2$/H$_2$O work-up. |
| 3 | 0.001 | 0.003 | Reaction conditions 1 hr at 100° C. One crystallization from CH$_3$OH/H$_2$O mixture, pH 9. |
| 3a | 0.001 | 0.003 | Reaction conditions same as Example 3. One crystallization from CH$_3$OH/H$_2$O mixture, pH 3. |
| 3b | 0.013 | 0.03 | Rerun of Example 3 except that reaction for 4 hrs at 50–70° C.; washed only with H$_2$O, no crystallization. |
| 3c | 0.005 | 0.007 | Reaction conditions same as Example 3b with crystallization from CH$_3$OH/H$_2$O mixture; no pH adjustment. |
| 3d | 0.001 | 0.005 | Same as 3 except pH 10–11. |
| 4a | 0.001 | 0.005 | See Example 4 for conditions, pH 9–10. |
| 4b | 0.002 | 0.008 | See Example 4 for conditions, pH adjusted to 5–6. |
| Polish Patent 144,765 | 0.087 | 0.009 | Reaction and isolation conditions of Polish patent described above; heating for 3 hrs at 40° C. |

*Used a Waters Model 244 liquid chromatograph described previously.
**These columns show the relative amounts of the respective impurity as measured by their absorbance values at 280 nm by previously described chromatographic analysis. The smaller the number, the smaller the amount of the respective impurity in the dichloride.

The dichloride obtained in accordance with the present invention has many uses. One of the more important uses to which this composition may be put is as an intermediate in the preparation of heat-resistant polyester resins which have many uses. For instance, the dichloride can be reacted with phthalic acid esters or certain phthalic acids themselves, such as dimethyl terephthalate, terephthalic acid, isophthalic acid, etc., to make polyester resins. An important use for the dichloride is in the preparation of flame and heat resistant polycarbonate resins by reacting the dichloride with precursor carbonating agents, such as phosgene, diphenyl carbonate, etc. The polymeric compositions derived from the reaction of the dichloride here described have many applications.

These polymeric compositions may be used to form fibers, films, or molded products. Thus, either by extrusion from melt or by depositing from solution, fibers derived from these polymeric compositions may be formed and used in the preparation of various textile materials designed for clothing and similar applications.

Various fillers may be incorporated in the polymeric compositions prior to molding thereof. Among such fillers may be mentioned glass fibers, carbon black, titanium dioxide, silica, mica, bentonite, etc. Molded products derived from such a mixture of ingredients can be used as gears, handles for cooking utensils, etc. The incorporation of abrasive particles such as carborundum, diamond powder, etc., makes molded products derived from such polymeric compositions useful as grinding wheels, etc. The addition of carbon, silicon carbide, powdered metal, conducting oxides, etc., to the polymeric compositions results in the so-called resistance or semiconducting paints which have many useful applications.

What we claim as new and desire to secure by Letters Patent of the United States is:

1. The process for dehydrohalogenating 1,1,1-trichloro-2,2-bis(4-hydroxyphenyl) ethane to form the dichloroethylene compound of the formula

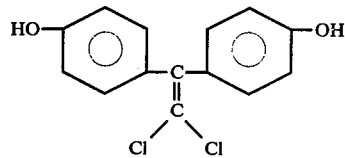

which process comprises (1) treating the aforesaid trichloroethane with from 3 to 20 moles anhydrous liquid ammonia per mole trichloroethane thereby to form a substantially pure dichloroethylene compound of the above formula, (2) removing unreacted ammonia, (3) dissolving the reaction product in an amount of a methanol/water mixture whose pH has been adjusted to from 3 to 11 sufficient to dissolve both the formed ammonium chloride and the aforesaid dichloroethylene compound, (4) heating the mixture of ingredients and then allowing the mixture to cool until precipitation of the dichloroethylene compound is accomplished and (5) isolating the precipitated dichloroethylene compound.

2. The process as in claim 1 wherein the dehydrohalogenation step is carried out under superatmospheric pressure and at a temperature of from about 10° to 125° C.

3. The process as in claim 1 wherein the treatment with the methanol/water mixture is at a pH below 7.

* * * * *